United States Patent
Hall (10) Patent No.: US 6,796,980 B2
(45) Date of Patent: Sep. 28, 2004

(54) SYSTEM AND METHOD FOR VALIDATING AND TROUBLESHOOTING ABLATION SYSTEM SET-UP

(75) Inventor: Jeffrey A. Hall, Birmingham, AL (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/990,960

(22) Filed: Nov. 21, 2001

(65) Prior Publication Data

US 2003/0097125 A1 May 22, 2003

(51) Int. Cl.⁷ ............................................... A61B 18/04
(52) U.S. Cl. ....................................................... 606/34
(58) Field of Search ............................. 606/27–52, 32, 606/33, 34, 35, 41, 42; 607/96, 98, 99

(56) References Cited

U.S. PATENT DOCUMENTS

| | | | | |
|---|---|---|---|---|
| 4,416,276 A | * | 11/1983 | Newton et al. ............... | 606/35 |
| 4,961,422 A | * | 10/1990 | Marchosky et al. .......... | 607/99 |
| 5,196,008 A | | 3/1993 | Kuenecke et al. | |
| 5,406,503 A | * | 4/1995 | Williams et al. ............ | 702/106 |
| 5,540,681 A | * | 7/1996 | Strul et al. .................... | 606/34 |
| 5,792,138 A | * | 8/1998 | Shipp ........................... | 606/38 |
| 5,931,835 A | * | 8/1999 | Mackey ........................ | 606/34 |
| 5,957,961 A | | 9/1999 | Maguire et al. | |
| 6,055,458 A | * | 4/2000 | Cochran et al. .............. | 700/17 |
| 6,409,722 B1 | * | 6/2002 | Hoey et al. .................... | 606/34 |

* cited by examiner

Primary Examiner—Michael Peffley
Assistant Examiner—Pete Vrettakos
(74) Attorney, Agent, or Firm—Fulwider Patton Lee & Utecht, LLP (57) ABSTRACT

A set-up algorithm verifies and troubleshoots the interconnection of devices within an ablation system including a power control system having a patient-return-electrode receptacle with a patient return electrode connected, a data port with a computer connected and an electrophysiological (EP) monitoring system receptacle with an EP monitoring system connected. The algorithm also verifies adequate contact between the patient return electrode and biological tissue. If a connection is not verified, the algorithm provides corrective actions to the system user and, upon user indication that corrective actions have been taken, retests the connection. Upon connection of a catheter to the power control system, the algorithm verifies the integrity of the catheter's power delivery and temperature sensing capabilities. After successful verification of all connections and catheter integrity, the algorithm allows the power control system to output power signals for ablation therapy.

1 Claim, 5 Drawing Sheets

SYSTEM AND METHOD FOR VALIDATING AND TROUBLESHOOTING ABLATION SYSTEM SET-UP

BACKGROUND OF THE INVENTION

1. Field of the Invention

The invention relates generally to ablation systems and, more particularly, to systems and methods for validating and troubleshooting the set-up of radio frequency ("RF") ablation systems.

2. Description of the Related Art

A typical RF ablation system includes a power control system, one or more patient return electrodes and a catheter having a one or more electrodes for transferring ablation energy from the power control system to biological tissue. Additional components may include a cardiac electrophysiological ("EP") monitoring system for recording intracardiac electrograms ("ECGs") through the catheter electrodes and a computer for viewing and logging ablation data.

During ablation system set-up the user manually connects each of the devices to the power control system and verifies the connections are proper. With respect to the patient return electrodes, e.g., backplates, this requires that the user connect the patient return electrode to the power control system to establish a return path for the RF current traveling through the tissue. Current market available patient return electrodes incorporate a self adhesive perimeter and conductive gel pad. The pad portion of the patient return electrode must be secured to the patient to complete the return path. During initial set up, adequate contact between the patient and the pad is verified visually by the user. After set up, the patient return electrodes are typically located under drapes thereby hiding them from visual view of the operator. At times inadequate contact between the pads and the patient may result from cable movement, perspiration, patient movement or a combination. In addition, the gel applied to the area between the pad and the patient may cause the pad to become displaced. Such post set-up conditions may go unnoticed by the user due to visual obstruction of the patient return electrodes.

With respect to the computer, the user must manually connect the computer cable, such as an RS232 cable, to the serial data port of the power control system and verify that the connection is proper. The computer typically includes some type of ablation related software that interacts with the power control system. For example, the computer may be programmed to receive ablation data, e.g., temperature, voltage, current, etc., from the power control system and log the data for future review and analysis. The computer may also display the ablation data. Even though the computer cable may be physically connected to the power control system, the communication link between the software and the power control system may not be established due to problems with computer communication parameters or the absence of the appropriate active communication software.

With respect to the cardiac EP monitoring system, commercially available systems have individual input connectors for displaying individual ECGs and physiological data on multiple channels. A typical ablation catheter, however, has a single multiple pin connector connecting to an interface breakout box with single pin connectors. The user must connect the catheter connector pins to the EP monitoring system pins in the correct pin sequence for the system to operate correctly and to properly display ECGs signal in the correct sequence. Mistakes are common and significant time is spent troubleshooting EP monitoring system connections. If EP monitoring system connections are improper or gains are not the same, there is a significant risk of an incorrect channel sequence or incorrect amplitude leading to misinterpretation of signals.

Given the number of devices within an ablation system and the external factors effecting the integrity of an ablation system, operators spend a significant amount of time verifying system set-up prior to performing ablation procedures. If set-up problems are detected, additional time is required to troubleshoot the system to locate the source of the problem.

Hence, those skilled in the art have recognized a need for an ablation system with the capability to validate ablation-system device interconnections and to troubleshooting invalid interconnections. The need for interactive troubleshooting capability to minimize procedure time and provide corrective actions has also been recognized. The invention fulfills these needs and others.

SUMMARY OF THE INVENTION

Briefly, and in general terms, the invention is directed to systems and methods for validating and troubleshooting the set-up of an ablation system.

In a first aspect, the invention relates to a method of troubleshooting an ablation system having at least one patient return electrode, a power control system adapted to output power signals, a computer, and a cardiac electrophysiological ("EP") monitoring system. The patient return electrode, computer and EP monitoring system are adapted to connect to the power control system at a patient-return-electrode receptacle, a data port and an EP-monitoring-system receptacle respectively. The patient return electrode is further adapted to contact biological tissue. The method includes verifying the connection between the power control system and the patient return electrode and verifying that adequate contact exists between the patient return electrode and the biological tissue. The method further includes verifying the connections between the power control system and the computer and between the power control system and the EP monitoring system. After successful verifications, the power control system is allowed to output power signals for ablation therapy.

In a detailed aspect, the patient-return-electrode receptacle includes a switch which, in the absence of an inserted connector, is open. Verifying the connection between the power control system and the patient return electrode includes confirming that the switch or circuit is closed. In a further detailed aspect, confirming that the switch is closed includes outputting a test signal to the input of the switch and monitoring the output of the switch for the signal. A still further detailed aspect of the method includes generating an error indication when the switch is open.

In another detailed facet, the patient return electrode includes at least two electrically isolated return electrode pads. Verifying adequate contact between the patient return electrode and the biological tissue includes measuring the impedance between the return pads and comparing the impedance to an expected value. In a further detailed facet, the method includes generating an error indication when the measured impedance is greater than the expected value.

In another detailed aspect, the data port includes a switch which, in the absence of an inserted connector or completed circuit, is open and verifying the connection between the power control system and the computer includes confirming that the switch is closed. In a further detailed aspect, confirming that the switch is closed includes outputting a test signal to the input of the switch and monitoring the output of the switch for the signal. In another further detailed aspect, verifying the connection between the power control system and the computer further includes establishing communication between the power control system and the computer. In a still further detailed aspect, establishing communication between the power control system and the computer includes polling the computer and waiting for an answer and verifying the presence, initialization and correct setting of appropriate software in the computer.

In another detailed facet, the power control system has a multiple pin EP-monitoring-system receptacle and the EP monitoring system includes an EP recorder having a plurality of inputs and a display for displaying ECG signals. Verifying connection between the power control system and the EP monitoring system includes outputting a signal of a given amplitude to each of the EP-monitoring-system pins in sequence and monitoring the EP recorder display for receipt of each signal in sequence. In a further detailed aspect, each of the signals is a pulse signal having substantially the same amplitude and verifying connection between the power control system and the EP monitoring system further includes monitoring the EP recorder for consistent amplitudes among each of the received signals and calibrating the EP monitoring system in accordance with the amplitude.

In another aspect, the invention relates to an ablation system including a power control system adapted to output power signals. The power control system includes a patient-return-electrode receptacle, a data port and an EP-monitoring-system receptacle. The ablation system further includes a patient return electrode adapted to connect to the patient-return-electrode receptacle, a computer adapted to connect to the data port and an EP monitoring system adapted to connect to the EP-monitoring-system receptacle. The ablation system also includes a processor that is programmed to verify the connection between the power control system and the patient return electrode; verify that there is adequate contact between the patient return electrode and the biological tissue and verify the connection between the power control system and the computer. The processor is also programmed to verify the connection between the power control system and the EP monitoring system and after successful verifications, allow the power control system to output power signals.

These and other aspects and advantages of the invention will become apparent from the following detailed description and the accompanying drawings which illustrate by way of example the features of the invention.

DETAILED DESCRIPTION OF THE PREFERRED EMBODIMENTS

Figure 1:
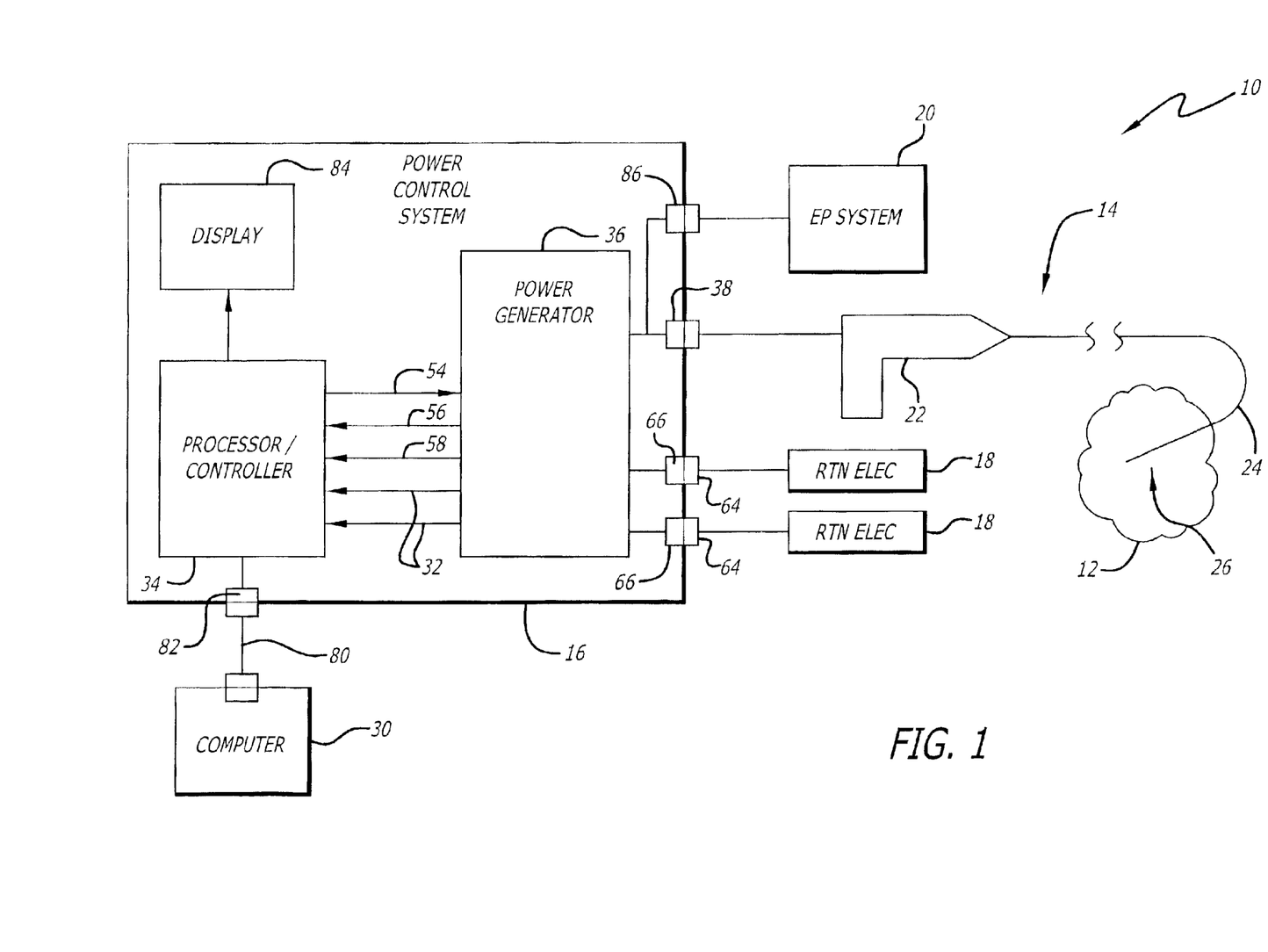
FIG. 1 is a schematic block diagram of an ablation system including a power control system, two patient return electrodes, a catheter system, a computer and an electrophysiological ("EP") monitoring system.

Turning now to the drawings, in which like reference numerals are used to designate like or corresponding elements among the several figures, in FIG. 1 there is shown an ablation system 10 for use in ablation therapy of a biological site 12, e.g., the atrium or ventricle of the heart. The ablation system 10 includes a catheter system 14, a power control system 16, a pair of patient return electrodes 18, an EP monitoring system 20 and a computer 30. The catheter system 14 provides RF current supplied by the power control system 16 to the biological site 12. The patient return electrodes 18 provide the return path for the RF current. The EP monitoring system 20 collects and displays electrograms from within the biological site through the electrodes at the distal end of the catheter, while the computer 30 displays, collects and logs ablation data.

Figures 2, 3:
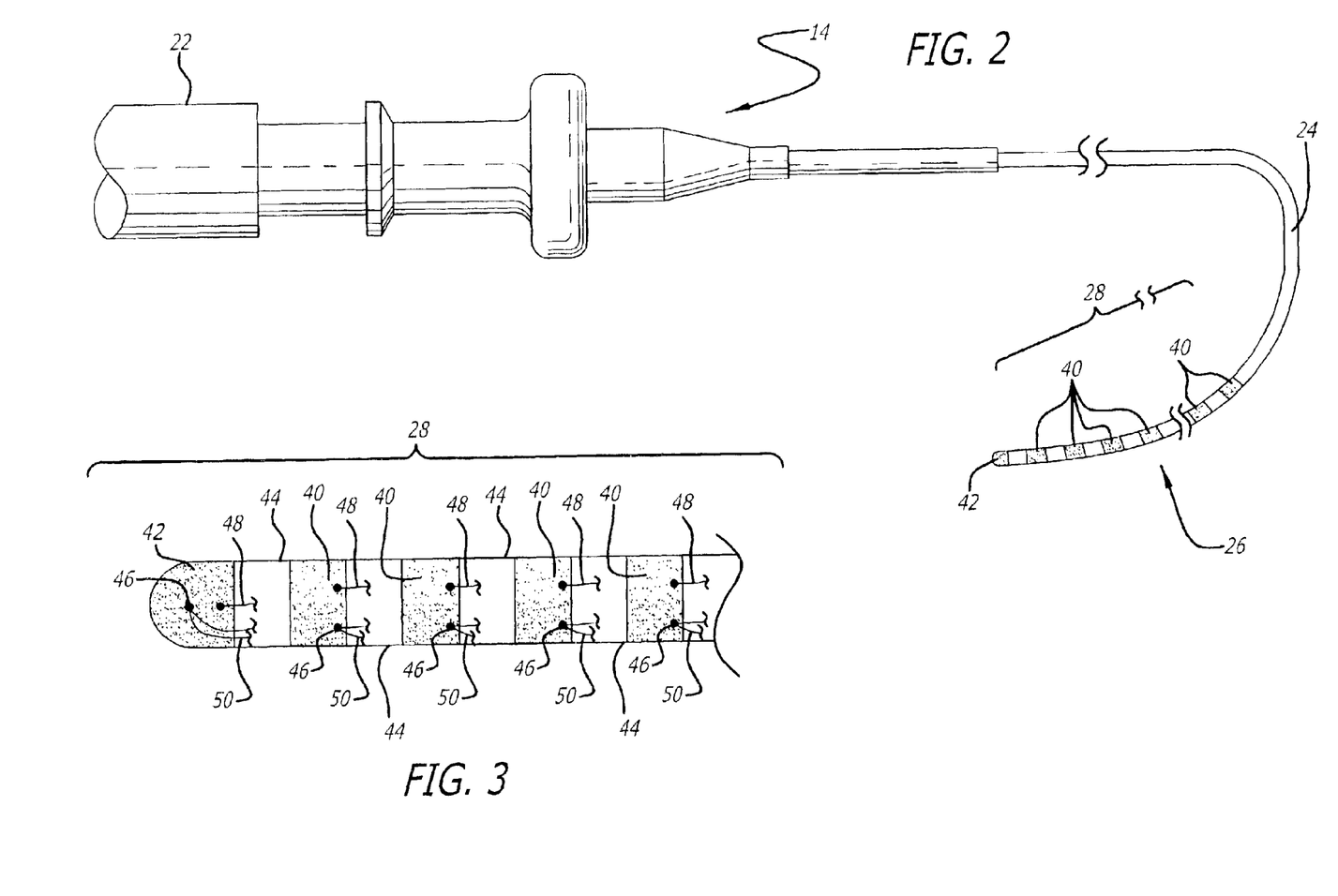
FIG. 2 is a diagram of the catheter system of FIG. 1 presenting more detail including a handle and a catheter shaft having a preformed distal segment carrying a linear array of electrodes.
FIG. 3 is a detailed schematic block diagram of a portion of the distal segment of the catheter system of FIG. 2, depicting a tip electrode and several band electrodes.

The catheter system 14 includes a handle 22 and a steerable catheter shaft 24 having a distal segment 26 that is capable of being percutaneously introduced into the biological site 12. As shown in FIGS. 2 and 3, the distal segment 26 of the catheter system 14 includes an electrode system 28. The electrode system 28 is shown in schematic form with the components drawn in more detail to more clearly illustrate the relationship between the components. A preferred embodiment of the electrode system 28 includes twelve band electrodes 40 arranged in a substantially linear array along the distal segment 26 of the catheter shaft 24. The electrode system 28 may include a tip electrode 42. (For clarity of illustration, only six band electrodes 40 are shown in FIG. 2 and only four band electrodes 40 are shown in FIG. 3 although as stated, a preferred embodiment may include many more.) The band electrodes 40 are arranged so that there is an electrically non-conductive space 44 between adjacent electrodes. In one configuration of the electrode system 28, the width of the band electrodes 40 is 3 mm and the space 44 between the electrodes is 4 mm. The total length of the electrode system 28, as such, is approximately 8 cm.

The band electrodes 40 are formed of a material having a significantly higher thermal conductivity than that of the biological tissue to be ablated. possible materials include silver, gold, chromium, aluminum, molybdenum, tungsten, nickel, platinum, and platinum/10% iridium. Because of the difference in thermal conductivity between the band electrodes 40 and the tissue, the electrodes cool off more rapidly in the flowing fluids at the biological site. The band electrodes 40 are sized so that the surface area available for contact with fluid in the heart, e.g., blood, is sufficient to allow for efficient heat dissipation from the electrodes to the surrounding blood. In a preferred embodiment, the band electrodes 40 are 7 French (2.3 mm in diameter) with a length of 3 mm and a thickness in the range of about 0.002 mm to about 0.010 mm.

Associated with the electrode system 28 are thermal sensors 46 for monitoring the temperature of the electrode system 28 at various points along its length. In one embodiment, each electrode 40, 42 has a thermal sensor 46 mounted to it. In another embodiment of the electrode system 28 a thermal sensor 46 is mounted on every other band electrode 40. Thus for a catheter having twelve electrodes, there are thermal sensors on six electrodes. In yet another embodiment of the electrode system 28 the odd numbered electrodes have one thermal sensor 46 while the even numbered electrodes have two thermal sensors. In yet another embodiment of the electrode system 28 the electrodes have two thermal sensors 46. In FIG. 3, which shows an embodiment having one thermal sensor for each electrode, there is shown a single power lead 48 for each electrode 40 to provide power to each electrode for ablation purposes and two temperature leads 50 for each thermal sensor 46 to establish a thermocouple effect. In another configuration (not shown), the power lead acts as one of the thermocouple leads thereby reducing the number of wires. Details of such configurations are disclosed in U.S. Pat. Nos. 6,042,580, 6,045,550 and 6,049,737 the disclosures of which are hereby incorporated by reference. In alternate embodiments, the thermal sensors 46 may include thermistors, RTDs and fluoroptic probes. The power leads 48 and thermocouple leads 50 travel the length of the shaft 24 and through the handle 22 to interface with the power control system 16 through a catheter receptacle 38.

With reference to FIG. 1, the power control system 14 includes a power generator 36, that may have any number of output channels through which it provides power to the electrodes of the electrode system 28. The operation of the power generator 36 is controlled by a processor/controller 34 which outputs control signals 54 to the power generator 36. The processor/controller 34 monitors the power provided by the power generator 36 over a power monitor line 56. In addition, the processor/controller 34 also monitors the temperatures of the electrodes within the electrode system 28 over a temperature monitor line 58. Based on the monitored power and temperature, the processor/controller 34 adjusts the operation of the power generator 36 to the electrodes, either collectively in groups or zones, or individually. Details of a multichannel power control system are disclosed in U.S. Pat. Nos. 6,050,994, 6,059,778 and 6,171,305, the disclosures of which are hereby incorporated by reference.

Figure 4:
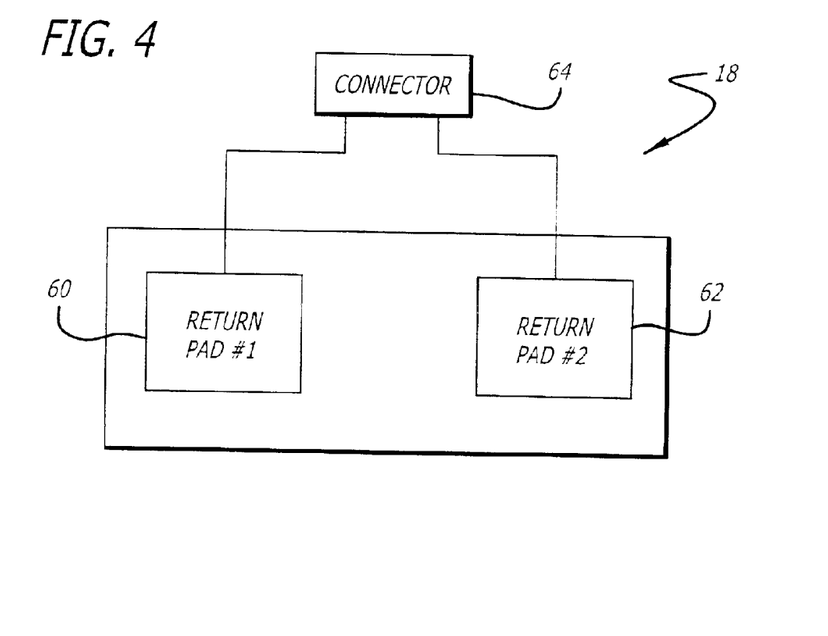
FIG. 4 is a schematic block diagram of the patient return electrode(s) of FIG. 1.

With reference to FIG. 4, in a preferred configuration of the ablation system 10, the patient return electrodes 18 are twin pad return electrodes such as Valleylab Inc., Patient Return Electrode, catalog # E7506. The patient return electrode 18 includes two electrically isolated return pads 60, 62. Each of the return pads 60, 62 are connected to a patient return electrode connector 64 that interfaces with the power control system 16 through a patient-return-electrode receptacle 66 (FIG. 1). As explained further below, the twin pad feature of the patient return electrode 18 is used to validate proper contact between the biological site and the patient return electrode. The processor/controller 34 monitors the connection and contact state of the patient return electrodes 18 over patient return electrode monitor lines 32.

Figure 5:
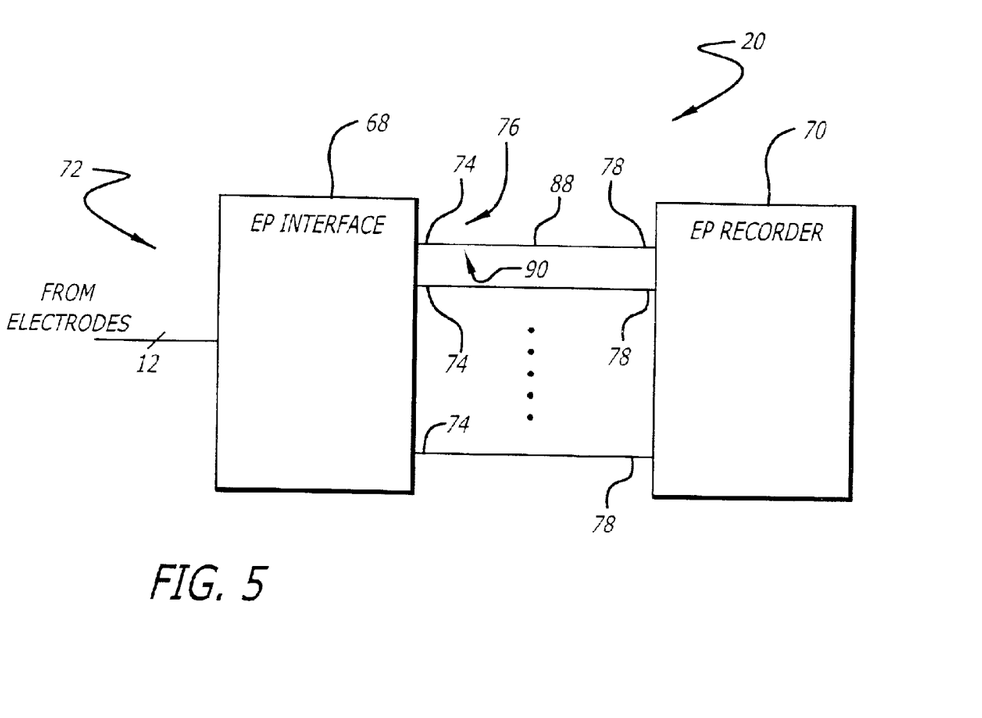
FIG. 5 is a schematic block diagram of the EP monitoring system of FIG. 1.

With reference to FIG. 5, the EP monitoring system 20 includes an EP interface 68 or breakout box and an EP recorder 70. At its input side 72, the EP interface 68 interfaces with the multiple pin connector of the catheter either indirectly through the power control system through an EP monitoring system 86 receptacle (as shown in FIG. 1) or directly (not shown). The EP interface 68 breaks out the multiple pin connector from the catheter into individual connectors 74 at its output side 76. These individual connectors 74 are connected to individual inputs 78 on the EP recorder 70 through leads 88. The electrograms from the electrodes are fed to the EP interface 68 where they are filtered before being fed to the EP recorder 70 where they are displayed. For a multi-electrode system, each electrode is individually displayed. In an alternate embodiment, filtering is done within the power generator 36 (FIG. 1).

With reference to FIG. 1, the computer 30 interfaces with the power control system 16 through a cable 80 connected to a data port 82, such as a RS232 port or other serial port. The processor/controller 36 outputs ablation data, including electrode temperature and power output voltage and current measurements, to the computer 30 over the cable 80. Software within the computer 30 receives the ablation data and logs it for future review and analysis. The data may also be displayed by the computer.

In accordance with the invention, the processor/controller 30 is programmed to execute an ablation system 10 set-up algorithm. Details of this algorithm are provided below. In general, however, the set-up algorithm verifies the interconnections between the power control system 16 and each of the patient return electrodes 18, computer 30, EP monitoring system 20 and, if present, the catheter system 14. The set-up algorithm also verifies additional ablation system 10 aspects. For instance, the set-up algorithm verifies that adequate contact exists between the patient-return-electrode pads and the biological site 12. With regard to the computer 30, the set-up algorithm verifies the presence of ablation software and the establishment of communication between the ablation software and the processor/controller 34. The set-up algorithm also assists in ensuring proper pin-to-pin connection between the catheter electrodes and the EP monitoring system 20.

The set-up algorithm also includes a series of interactive troubleshooting routines which provide real-time solutions to detected problems. The troubleshooting routines may be co-located with the set-up algorithm in the processor/controller 34. In this case, the troubleshooting routines output solution steps for viewing on the power control system display 84. After the user completes the indicated solution steps, the set-up algorithm confirms correction of the problem.

Alternatively, the troubleshooting routines may be located in the computer 30. In this case, when a problem is detected by the set-up algorithm, an error code is generated and output from the processor/controller 34 to the computer 30. At the computer 30, the error code invokes the appropriate troubleshooting routine which starts a graphical display demonstrating the error point in the setup or operation of the ablation system 10. The troubleshooting routines then starts a window with multiple real-time solution steps. After user intervention, the troubleshooting routine sends a signal to the processor/controller 34 indicating the solution steps are complete and the set-up algorithm confirms correction of the problem.

Figure 6A:
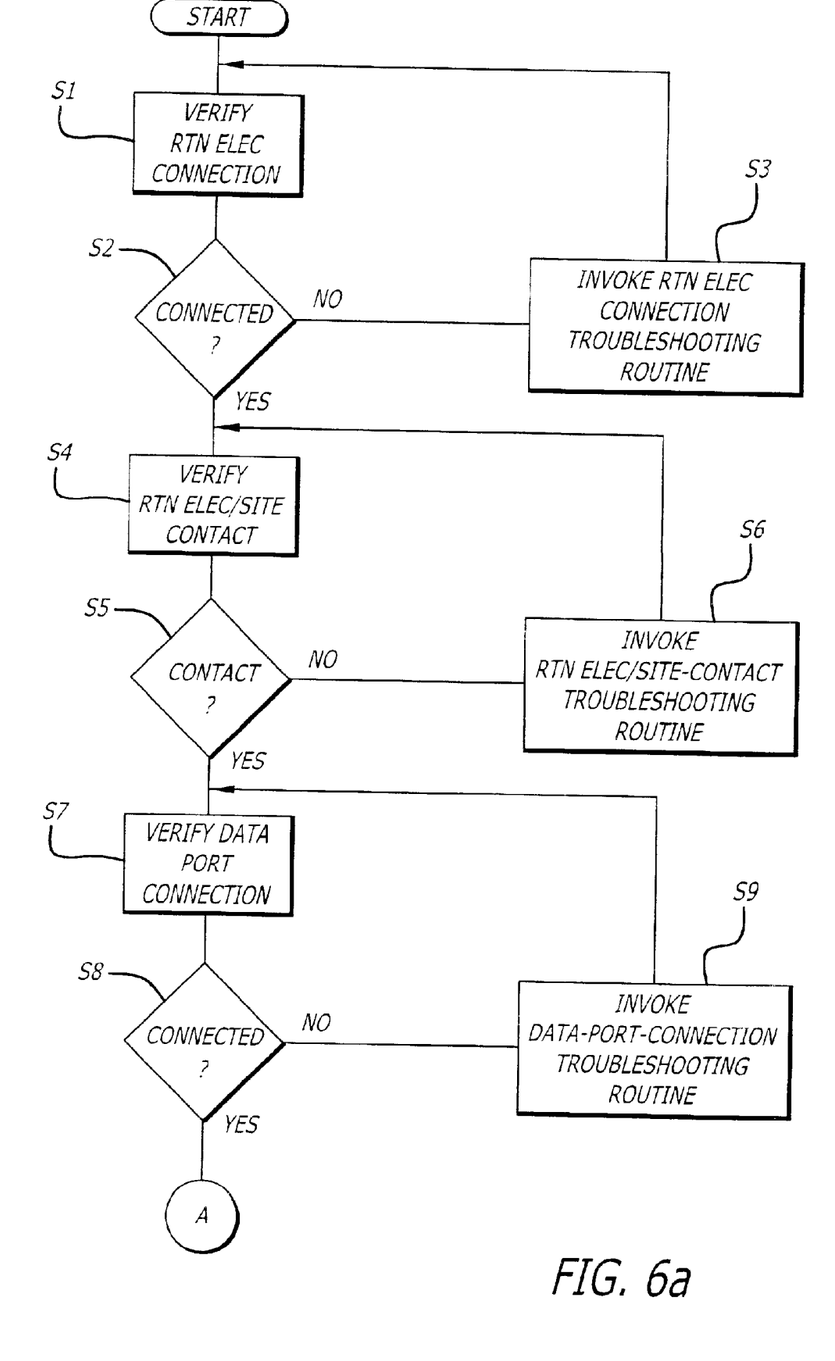
FIGS. 6a and 6b form a flow chart of the operation of the set-up validation and troubleshooting system used to test the ablation system of FIG. 1.
Figure 6B:
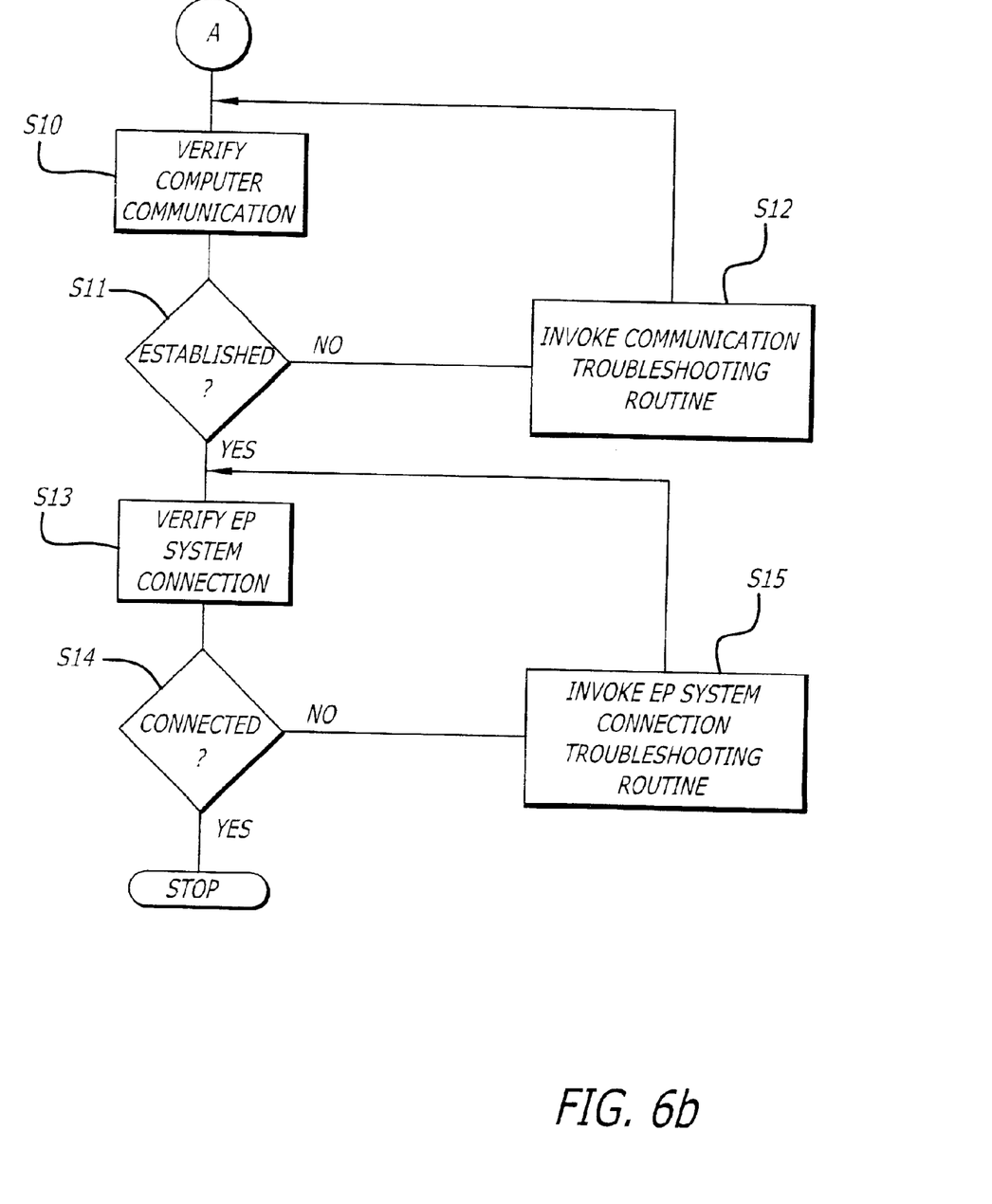

The operation of the set-up validation and troubleshooting system is described with reference to FIGS. 6a and 6b. In general, FIGS. 6a and 6b show a flow chart that sets forth not only the operation of the set-up validation and troubleshooting system, but also the architecture and functionality of the software-based system. The blocks of the flowchart can be viewed as sections of code.

The set-up algorithm is invoked manually through the front panel of the power control system 16. The processor/controller 34 executes the set-up algorithm. At step S1, the set-up algorithm verifies that the patient return electrodes 18 are connected to the patient-return-electrode receptacles 66 of the power control system. In one embodiment, each of the patient-return-electrode receptacles 66 includes a switch or circuit (not shown) which, in the absence of an inserted connector, is open. To verify the connection between the patient return electrode 18 and the patient-return-electrode receptacle 66, the set-up algorithm confirms that the switch is closed by outputting a patient-return-electrode/connection verification signal to the input of the switch and monitoring for the return of the signal through the output of the switch.

At step S2, if the patient-return-electrode/connection verification signal is received, connection is confirmed and the set-up algorithm proceeds to step S4 where it verifies adequate contact between the patient-return-electrode pad and the biological site 12 undergoing treatment. If the patient-return-electrode-connection verification signal is not received, connection is not confirmed and the set-up algorithm generates an error code, which at step S3, invokes a patient-return-electrode/connection troubleshooting routine.

In one embodiment, the patient-return-electrode/connection troubleshooting routine is co-located with the set-up algorithm in the processor/controller 34. When invoked, the patient-return-electrode/connection troubleshooting routine displays corrective action instructions to the user, either through the power control system display 84 or, if available, the monitor on the computer 30. If the computer 30 is available, a patient-return-electrode/connection troubleshooting subroutine stored within the computer is invoked. This subroutine, through a graphical user interface on the computer monitor, indicates the error point, e.g., "open circuit" or "open switch", "patient return electrode not connected" and corrective actions, e.g., "check cable connection", "if not connected, connect", "if connected, disconnect and check cable connector and patient-return-electrode receptacle pins", "reconnect cable".

If only the power control system display 84 is available, a patient-return-electrode/connection troubleshooting subroutine stored within the processor/controller 34 is invoked and similar type messages are displayed in accordance with the capabilities of the display 84. In another embodiment a green LED (not shown) on the power control system above the patient-return-electrode receptacle 66 instantly verifies proper cable connection. Once the corrective actions are completed, the user notifies the patient return electrode-connection troubleshooting routine through a user interface, e.g., front panel control on power control system or computer keyboard. The set-up algorithm is reinvoked and operation returns to step S1 to verify patient return electrode connection. Steps S1, S2 and S3 are repeated as necessary depending on the number of patient return electrodes 18.

At step S4, the set-up algorithm verifies adequate contact between the patient return electrode pad and the biological site 12. With reference to FIG. 4, the set-up algorithm does this by obtaining a measurement of the impedance between the two return pads 60, 62 and comparing the impedance to an expected value. The impedance measurement is obtained passively through circuitry within the processor/controller 34 which interfaces with the patient return electrode 18 through the patient-return-electrode monitoring lines 32 and the patient return electrode connection previously verified in step S1. preferably, the patient return electrode pad is secured to the biological site 12 such that the entire surface area of the two return pads 60, 62 is in contact with the site. The expected impedance value is within the range of approximately 80 ohms and 120 ohms. A measured impedance value greater than the expected value is indicative of inadequate contact. In another embodiment, the processor/controller 34 repeatedly samples the impedance value and monitors the samples for a high standard deviation, indicative of inadequate contact. This is based on the recognition that the impedances measured across a secure patient return electrode are substantially consistent, i.e., they do not deviate significantly from an average value, while impedances measured across a loose patient return electrode are inconsistent due to periodic and repeated patient movement relative to the return electrode, such as that caused by patient breathing, and accordingly have a high standard deviation.

At step S5, if the measured impedance is less than the expected impedance or the standard deviation is indicative of adequate contact, contact is confirmed and the set-up algorithm proceeds to step S7 where it verifies connection between the data port 82 on the power control system 16 and the computer 30. If the measured impedance is equal to or greater than the expected impedance or has a high standard deviation, patient-return-electrode/site contact is not confirmed and the set-up algorithm generates an error code, which at step S6, invokes a patient-return-electrode/site-contact troubleshooting routine.

Like the previously described patient-return-electrode/connection troubleshooting routine, the patient-return-electrode/site-contact troubleshooting routine displays corrective action instructions to the user, either through the power control system display 84 or, if available, the monitor on the computer 30. If the computer 30 is available, a patient-return electrode/site-contact troubleshooting subroutine stored within the computer is invoked. This subroutine, through a graphical user interface on the computer monitor, indicates the error point, e.g., "impedance out of range" and corrective actions, e.g., "check electrode-patient contact", "secure pad to patient."

If only the power control system display 84 is available, a patient-return-electrode/site-contact troubleshooting subroutine stored within the processor/controller 34 is invoked and similar type messages are displayed on the display 84. In one embodiment, a red LED (not shown) on the power control system indicates inadequate patient return electrode contact. Once the corrective actions are completed, the user notifies the troubleshooting routine through a user interface. The set-up algorithm is reinvoked and operation returns to step S4 to verify patient-return-electrode/site contact. Steps S4, S5 and S6 are repeated as necessary depending on the number of patient return electrodes 18.

At step S7, the set-up algorithm verifies that the data port 82 on the power control system 16 has a data connector inserted therein. In one embodiment, the data port 82 includes a switch or circuit (not shown) which, in the absence of an inserted connector, is open. To verify the insertion of a data connector in the data port 82, the set-up algorithm confirms that the switch is closed by outputting a data-port-connection verification signal to the input of the switch and monitoring for the return of the signal through the output of the switch.

At step S8, if the data-port-connection verification signal is received, connection is confirmed and the set-up algorithm proceeds to step S10 where it verifies communication between the computer software and the processor/controller 34. If the data-port-connection verification signal is not received, connection is not confirmed and the set-up algorithm generates an error code, which at step S9, invokes a data-port-connection troubleshooting routine.

When invoked, the data-port-connection troubleshooting routine displays corrective action instructions to the user, either through the power control system display 84 or, if available, the monitor on the computer 30. If the computer 30 is available, a data-port-connection troubleshooting subroutine stored within the computer is invoked. This subroutine, through a graphical user interface on the computer monitor, indicates the error point, e.g., "data-port connector not connected" and corrective actions, e.g., "check cable connection", "if not connected, connect", "if connected, disconnect and check cable connector and patient-return-electrode receptacle pins", "reconnect cable".

If only the power control system display 84 is available, a data-port-connection troubleshooting subroutine stored within the processor/controller 34 is invoked and similar type messages are displayed on display 84. Once the corrective actions are completed, the user notifies the troubleshooting routine through a user interface; the set-up algorithm is reinvoked and operation returns to step S7 to verify data port connection.

Once data port connection is verified, the set-up algorithm, at step S10, establishes communication between the processor/controller 34 and the computer 30 by polling the computer for the presence of the appropriate ablation software and waiting for an answer. At step S11, if an answer is received, communication is confirmed and the set-up algorithm proceeds to step S13 where it verifies EP monitoring system connection. If communication between the processor/controller 34 and the computer 30 is not confirmed, the set-up algorithm generates an error code, which at step S12, invokes a communication troubleshooting routine.

When invoked, the communication troubleshooting routine displays corrective action instructions to the user, either through the power control system display 84 or, if available, the monitor on the computer 30. If the computer 30 is available, a communication troubleshooting subroutine stored within the computer is invoked. This subroutine, through a graphical user interface on the computer monitor, indicates the error point, e.g., "data communication device not answering" and corrective actions, e.g., "check cable connection at computer", "if not connected, connect", "if connected, reboot computer", "reconnect cable", "check for appropriate software". Further examples include: "communications unable to initialize, recycle power control system and restart data program", "communications initialized unable to communicate, check for correct baud rate and correct serial data port", "unable to find serial data port, confirm correct active serial port in computer setup."

If only the power control system display 84 is available, a communication troubleshooting subroutine stored within the processor/controller 34 is invoked and similar type messages are displayed on the display 84. Once the corrective actions are completed, the user notifies the troubleshooting routine through a user interface. The set-up algorithm is reinvoked and operation returns to step S10 to confirm communication between the processor/controller 34 and the computer 30.

At step S13 the set-up algorithm verifies EP monitoring system connection by sequentially outputting a pulse signal to each pin of the EP-monitoring-system receptacle 86 (FIG. 1) on the power control system 16. For a multiple channel ablation system, the pulses are output in sequence starting from the channel 1 pin, with a slight time delay between pulses, such as one second. If the lead 88 (FIG. 5) connections between the EP interface 68 and EP recorder 70 is correct, the pulses are displayed on the EP recorder 70 as a progressive sequence starting from channel 1 and ending with the last channel. In one embodiment, the sequence of pulse signals repeats until correct connection is confirmed by the user. This allows the user to reconnect leads 88 as necessary until proper connection is achieved. In another embodiment, the sequence of pulses repeat a set number of times and may be repeated further upon user request. The pulses are further used to calibrate the EP recorder 70. In this regard, each pulse within the sequence has the same amplitude. Knowing this, the gain for each channel on the EP recorder 70 may be set by the user so that each channel display has the same amplitude.

With respect to the EP monitoring system, visual conformation may be necessary to validate the EP monitoring system configuration settings since these affect the amplitude of the displayed signal and the invocation of specific noise filter settings and notch filters and are only visual on the EP recorder. A computer prompt could be used initially to prompt confirmation of equal settings (amplitude and filter settings) for each catheter electrode channel. prompts could also display the common settings and could be user adjustable (via a configuration file) to allow for different manufacturers of EP monitoring systems and variation in setup and configuration.

At step S14, if proper EP monitoring system connection is confirmed by the user the set-up algorithm proceeds to step S16 where it generates a message that the system is ready for ablation. If EP monitoring system connection is not confirmed, the set-up algorithm generates an error code, which at step S15, invokes an EP monitoring system connection troubleshooting routine.

When invoked, the EP monitoring system connection troubleshooting routine displays corrective action instructions to the user, either through the power control system display 84 or, if available, the monitor on the computer 30. If the computer 30 is available, an EP monitoring system connection troubleshooting subroutine stored within the computer is invoked. This subroutine, through a graphical user interface on the computer monitor, indicates the error point, e.g., "EP connection error" and corrective actions, e.g., "check lead connections", "if not connected, connect", "if connected, disconnect and check lead connectors", "reconnect lead", "check lead connection sequence."

If only the power control system display 84 is available, an EP-monitoring-system connection troubleshooting subroutine stored within the processor/controller 34 is invoked and similar type messages are displayed on the display 84. Once the corrective actions are completed, the user notifies the troubleshooting routine through a user interface. The set-up algorithm is reinvoked and operation returns to step S13 to verify EP monitoring system connection.

As previously mentioned, execution of the set-up algorithm may be initiated manually though the front panel of the power control system 16. Alternatively, it may be initiated automatically, through connection of a catheter system 14 to the catheter receptacle 38 of the power control system 16. Automatic initiation as such ensures that the set-up algorithm is run prior to any ablation procedure. The catheter receptacle 38 includes a switch (not shown) which closes upon insertion of a catheter connector to provide a signal to the processor/controller 34. Upon receipt of this signal, the processor/controller 34 initiates the set-up algorithm. In this instance, the set-up algorithm verifies the integrity of the catheter along with all other previously described verifications.

For a catheter configured such that the power lead acts as one of the thermocouple leads as disclosed in U.S. Pat. Nos. 6,042,580, 6,045,550 and 6,049,737, the catheter integrity check includes testing of the power lead 48 and thermocouple lead 50 connection between the catheter electrodes and the pin connector at the proximal end of the catheter system 14. The electrode system 28 is maintained at a temperature different then that of the handle, where a cold junction reference temperature is measured. The temperature difference forces each thermocouple 46 to output a voltage indicative of the temperature at the thermocouple. This voltage is output by the catheter and received by the processor/controller 34 over the temperature monitor line 58. The set-up algorithm verifies the presence of a voltage for each thermocouple 46. The absence of an output voltage for any particular thermocouple 46 is indicative of a faulty lead 48, 50 connection for that thermocouple. Because one of the leads for the thermocouple 46 as functions as a power lead 48, the output of a voltage from a thermocouple also confirms proper power lead connection.

Once the set-up algorithm is complete and all verification steps have been satisfied, the algorithm allows the power control system 16 to proceed with the ablation procedure. If any of the verification steps are not satisfied, the algorithm prevents the power generator from outputting power to the electrodes. While the foregoing description of the set-up algorithm has focused on the use of the algorithm to verify and troubleshoot ablation system set-up prior to ablation therapy, the algorithm may be used during ablation to periodically monitor device connections. In this regard, the set-up algorithm may recycle automatically when an error is encountered until that error is corrected. The computer monitor or power control system display is updated regularly and shows the error correction and the successful completion of the setup algorithm. For example, the algorithm may periodically repeat step S4 (verification of patient return electrode/biological site contact) to ensure the patient return electrodes are properly positioned throughout the ablation procedure.

Regarding the graphical user interface, the computer may display, for example, a graphical representation of the system similar to that shown in FIG. 1. If an error in diagnostics occurs, those system components associated with the error may flash in red. For example, if a faulty connection between the patient return electrode and the power control system is detected, the connector 64 and receptacle 66 may flash in red. This indication may also be accompanied by a flashing red color coded error message. If the set up associated with a component is successful, the components may be displayed in solid green color along with a coded symbol for completed successfully diagnostics. In addition, a graphical flow diagram may be included that indicates each step of the set-up algorithm in sequence. The flow diagram includes a error/success indicator for each step in the sequence.

With respect to the EP monitoring system, visual conformation may be necessary to validate the EP monitoring system configuration settings since these affect the amplitude of the displayed signal and the invocation of specific noise filter settings and notch filters and are only visual on the EP recorder. A computer prompt could be used initially to prompt confirmation of equal settings (amplitude and filter settings) for each catheter electrode channel. prompts could also display the common settings and could be user adjustable (via a configuration file) to allow for different manufacturers of EP monitoring systems and variation in setup and configuration.

In one embodiment, the set-up validation and troubleshooting system is implemented in software that is stored in ROM of the processor/controller 34. In alternate embodiments, the software may be stored, transported, and/or utilized while residing on any computer-readable medium for use by or in connection with any suitable computer-based system. In the context of this document, a computer readable medium is an electronic, magnetic, optical or other physical device or means that can contain or store a computer program for use by or in connection with a computer-based system.

The system and method thus described may be easily adapted for use in other ablation systems and is in no way limited to cardiac RF ablation systems. The system and method may find adaptation in any ablation system in which power control systems and various external systems and equipment must interface with each other and with the patient. Other examples of ablation energy sources for power control systems are ultrasound, laser, microwave and cyrogenic energy, each of which results in the ablation of biological tissue.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. An ablation system comprising:

a power control system having a multiple pin electrophysiological (EP) monitoring system receptacle having a first pin and last pin, the power control system adapted to output power signals;

an EP monitoring system adapted to connect to the EP-monitoring-system receptacle, the EP monitoring system including an EP recorder having a plurality or inputs and a display for displaying ECG signals; and a processor programmed to verify connection between the power control system and the EP monitoring system by outputting a signal to each of the EP-monitoring-system receptacle pins in sequence and displaying the pulses on the EP monitoring system display as a progressive sequence staring with the first pin an ending with the last pin wherein the processor is further programmed to prevent the output of power signals in the absence of the verification of the connection between the power control system and the EP monitoring system.

* * * * *

UNITED STATES PATENT AND TRADEMARK OFFICE
CERTIFICATE OF CORRECTION

PATENT NO.    : 6,796,980 B2
DATED         : September 28, 2004
INVENTOR(S)   : Jeffrey A. Hall It is certified that error appears in the above-identified patent and that said Letters Patent is hereby corrected as shown below:

Column 4,
Line 47, delete "possible" and insert -- Possible --.

Column 7,
Line 54, delete "preferably" and insert -- Preferably --.

Column 10,
Line 11, delete "prompts" and insert -- Prompts --.

Column 11,
Line 53, delete "prompts" and insert -- Prompts --.

Column 12,
Line 40, delete "or" and insert -- of --.
Line 47, delete "staring" and insert -- starting --.

Signed and Sealed this

Twenty-eighth Day of June, 2005

JON W. DUDAS
*Director of the United States Patent and Trademark Office*